US005798117A

United States Patent [19]

New et al.

[11] Patent Number: 5,798,117
[45] Date of Patent: Aug. 25, 1998

[54] METHOD OF REDUCING MICROORGANISM ADHESION

[75] Inventors: Roger R C New, London; Stephen A Charles, Oxon; Ewan J Campbell, Middlesex, all of Great Britain

[73] Assignee: Biocompatibles Limited, Middlesex, United Kingdom

[21] Appl. No.: 720,919

[22] Filed: Oct. 7, 1996

Related U.S. Application Data

[63] Continuation of Ser. No. 331,566, filed as PCT/GB93/00852 published as WO93/21970, abandoned.

[30] Foreign Application Priority Data

Apr. 24, 1992 [GB] United Kingdom ............... 9208950
Nov. 16, 1992 [GB] United Kingdom ............... 9224031

[51] Int. Cl.$^6$ .................. A61L 15/00; A61K 31/685; B63B 35/00; A61C 3/00
[52] U.S. Cl. .................. 424/445; 514/78; 114/270; 106/35; 433/3; 433/229
[58] Field of Search .................. 424/450, 445, 424/443; 514/78; 523/122; 114/270, 67 A; 106/243, 35; 433/3, 229

[56] References Cited

U.S. PATENT DOCUMENTS 4,459,362  7/1984  Yabusaki .................. 436/536
5,411,948  5/1995  Lingwood ................. 514/78

FOREIGN PATENT DOCUMENTS

| 0032622 | 7/1981 | European Pat. Off. |
| 0140854 | 5/1985 | European Pat. Off. |
| 8602933 | 5/1986 | WIPO |
| 8800956 | 2/1988 | WIPO |
| 9100745 | 1/1991 | WIPO |
| 9113639 | 9/1991 | WIPO |

*Primary Examiner*—Gohamudi S. Kishore
*Attorney, Agent, or Firm*—Sughrue, Mion, Zinn, Macpeak & Seas, PLLC

[57] ABSTRACT

A method of reducing the extent to which microorganisms, particularly bacteria, will adhere to a surface, which comprises providing a surface having pendant groups of formula (I), in which each group R is the same or different and is alkyl of 1 to 4 carbon atoms and a is from 1 to 4, use of compounds containing a group of formula (I) in reducing the extent to which microorganisms would adhere to a surface and use of articles comprising such surfaces in environments susceptible to microorganism adhesion. The method has application in a wide variety of industrial or domestic fields wherever it is desirable to prevent growth of microorganisms as well as in the medical field.

17 Claims, No Drawings

METHOD OF REDUCING MICROORGANISM ADHESION

This is a Continuation of application Ser. No. 08/331,566 filed Dec. 20, 1994 now abandoned, which application is a 371 of PCT/GB93/00852 filed Apr. 23, 1993.

The present invention relates to a new method of reducing the extent to which microorganisms will adhere to a surface. It also relates to the use of certain compounds in reducing the adhesion of microorganisms to a surface.

In many areas of technology the adhesion and consequent growth of microorganism such as bacteria, yeast, algae or fungi on surfaces can cause severe problems. Thus the adhesion of bacteria can cause malfunctions in machinery where for example the bacteria fouls the flow of a liquid over a solid surface; this can lead to an increase in drag and possibly blockage of the flow of liquid. Prolonged growth of microorganisms on a surface may moreover lead to corrosion, either by altering the pH or redox environment at the surface or by biodegradation of organic materials.

In addition the growth of microorganisms on a surface can pose a health hazard. Where a material is used as an optical material bacterial adhesion may reduce optical quality and thus performance.

Thus there are a wide variety of industrial and domestic applications where bacterial, algal, yeast or fungal adhesion may have an adverse effect. These include human and veterinary medicine, ophthalmology, wound dressings, dentistry, bioseparations, marine and freshwater shipping, transport of fluids through piping—e.g. in the oil industry, optics, optical and electronic communications systems, aviation and aeronautics, the food and drink industry, laboratory equipment, agricultural machinery, storage containers and packaging, fermentation processes and air-conditioning systems.

One specific area in which microorganism adhesion is a particular problem is human and veterinary medicine. Bacterial adhesion to and colonisation of prostheses inserted into the body for example intravenous, intra-arterial, intra-peritoneal and urinary catheters presents a serious clinical problem. In-dwelling catheters are the single most important source of hospital acquired infection, the clinical symptoms ranging from slight peripheral phlebitis to lethal septicaemia with multiple organ abscesses. Chemotherapeutic treatment of these infections is very difficult, and usually requires removal of the catheter. Even in cases where the patient remains healthy, bacterial colonisation can lead to build up of a biofilm with attendant mineral deposition, leading to blockage, and hence malfunction of the catheter. These problems may be alleviated by constructing catheters of material which does not cause bacteria to adhere to its surface.

Compounds which contain pendant phosphoryl choline groups mimic the structure of phospholipids which are a principal component in the cell membrane of all cells. Compounds containing such groups are known to have haemocompatibilising properties and to reduce the adhesion of blood platelets and consequent coagulation of blood at a surface which has been treated with them or is formed from them. Similarly such compounds are known to be useful in reducing protein adsorption at a surface; thus hydrogel polymers of compounds containing such groups have been found to be useful for making contact lenses which exhibit reduced protein absorption.

These uses have been described in EP-A-32,622, EP-A-157,469, WO-A-86/02933, WO-A-88/00956, WO-A-91/13639, WO-A-92/07885, WO-A-92/06719, WO-A-92/07858, WO-A-92/21386, WO-A-93/05081 and WO-A-93/01221.

We have now found that compounds which contain such a phosphoryl choline headgroup or close analogue thereof, are able to reduce the tendency of microorganisms to adhere to and grow on surfaces. They may also be used more generally to reduce cellular adhesion at a surface. Such use is neither disclosed nor suggested in the above-mentioned documents.

Materials which comprise such groups at their surface therefore have potentially wide utility wherever the growth of microorganisms such as bacteria, algae, yeast and fungi, paticularly bacteria, occurs and is undesirable. Such compounds may therefore be used in both the medical field and in other applications in industrial or domestic wherever it is desirable to prevent the growth of such microorganisms.

The present invention therefore provides a new method of reducing the extent to which microorganisms will adhere to a surface, which comprises providing a surface having pendant groups of formula (I):

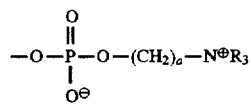

in which each group R is the same or different and is alkyl of 1 to 4 carbon atoms and a is from 1 to 4, preferably 2 to 4.

The invention further provides the use of compounds containing a group of formula (I) in reducing the extent to which microorganisms will adhere to a surface and the use of articles comprising such surfaces in environments susceptible to microorganism adhesion.

A surface having pendant groups of formula (I) may be provided by using a material the bulk and surface of which comprises such groups. Alternatively pendant groups of formula (I) may be provided by treating, for example coating, a substrate with one or more compounds containing a group of formula (I). Such surface treatments may be bound to the surface for example by physisorption (strong secondry valence interaction at a surface without formation of covalent bonds), by covalent bonding or by ionic bonding to reactive groups at the surface. Preferably the pendant groups are provided by treating a substrate with one or more compounds containing a group of formula (I) and rather than by using a compound containing a group of formula (I) to form a bulk material.

In one specific embodiment of the invention the growth of bacteria which adhere to a surface is reduced.

In compounds containing a group of formula (I) it is preferred that all the R group are same, and more preferred that all the R groups are methyl groups. It is also preferred that a is 2.

In the most preferred case, i.e. when a is 2 and all the groups R are methyl, the group of formula (I) is a phosphoryl choline group.

Compounds containing a group of formula (I) may be either non-polymeric or polymeric; if polymeric then they may be a homopolymer or copolymer of a polymerisable compound containing a group of formula (I). Alternatively a polymeric compound containing groups of formula (I) may be a polymer onto which groups of formula (I) have been grafted. Non-polymeric compounds containing a group of formula (I) may be phospholipids or their analogues or other non-polymeric compounds containing a group of formula (I), such as compounds capable of reacting with reactive groups at a surface to provide covalent attachment of groups of formula (I) to the surface.

Materials comprising surfaces with such pendant groups may in addition be used to provide means for the attachment of a variety of ligands to a material. The term ligand includes, but is not limited to, specific binding agents such as immunoglobulins and associated fragments thereof such as those useful for affinity separation and diagnostic applications, photosensitive and chemosensitive moieties such as those useful for detector and sensor applications and therapeutic agents, such as peptide fragments useful for clinical applications. Other ligands include peptide fragments which may be chemically linked to a surface, such as fragments which induce cell attachment and may therefore be used to allow cell seeding at the surface.

Means for the attachment of such ligands may be provided by compounds containing the group of formula (I) or, alternatively, they may be provided by additional compounds attached to the surface as well as compounds containing the group of formula (I). In particular, means for the attachment of such ligands may be provided by groups which contain an amine, hydroxyl or carboxylic acid group, or an activated derivative thereof. Such groups may optionally be in the form of a suitable salt and may, where necessary, be attached to a spacer group, such as alkylene of 1 to 12 carbon atoms, of sufficient length to allow the reactive group to interact with its binding partner on the ligand.

It will be appreciated that where it is desired to control the number of sites of attachment of such a ligand to a surface then a mixture may be used of compounds containing a group of formula (I) suitable for attachment to a ligand and containing a group of formula (I) not suitable for such attachment. Alternatively a copolymer of two such polymerisable compounds one of which contains a group of formula (I) and one of which provides a site for attachment of a ligand, may be used.

A. Phospholipids and analogues thereof containing a group of formula I

A.1 One type of phospholipid containing a group of formula (I) which may be used in the present invention is fatty acid diesters of phosphatidyl choline and fatty ether analogues thereof. Analogues thereof which may be used include diesters containing a different group of formula (I).

The fatty acid diesters of phosphatidyl choline which may be used in the process of the invention include esters of saturated and unsaturated fatty acids and may be pure single compounds such as dipalmitoyl phosphatidyl choline (DPPC) and dimyristoyl phosphatidyl choline (DMPC), mixtures of such compounds and purified natural products such as fatty acid diesters of phosphatidyl choline from egg yolk or soya bean lecithin. Mixed diesters of phosphatidyl choline may be used.

Preferably the fatty acid side chains will be straight as opposed to branched and will have from 2 to 26, for example 12 to 20, carbon atoms. Purified natural products may contain a small proportion of components other than fatty acid diesters of phosphatidyl choline but these should not be present in sufficient amount to impair the ability of the coating to reduce adhesion of microorganisms.

Corresponding diethers may alternatively be used.

Fatty acid diesters or diethers of phosphatidyl choline or other groups of formula (I) may be used to coat hydrophobic substrates such as PVC, polyethylene or polypropylene. The coating may be applied using a solution of the diester in an organic solvent and the solvent subsequently removed to leave a coating of fatty acid diester of phosphatidyl choline which is believed to be adhered to the substrate by physisorption. This technique is described in more detail in our patent application WO-A-92/06719 the contents of which are incorporated herein by reference.

A.2 Further phospholipid analogues which may be used to treat surfaces according to the present invention are the diacetylenic phospholipids of the formula (II)

in which Z is a group of formula (I) as hereinbefore defined and wherein at least one of $Q^1$ and $Q^2$ is a group of the formula (III)

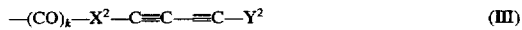

wherein k is 0 or 1, $X^2$ is an aliphatic or cycloaliphatic group, $Y^2$ is H or a monovalent aliphatic or cycloaliphatic group, the total number of carbon atoms in $X^2$ and $Y^2$ in each $Q^1$ and/or $Q^2$ being 8 to 26, preferably 20 to 26, and the other of $Q^1$ and $Q^2$ is either (a) the same or a different group of formula (VII) or (b) is an aliphatic or cycloaliphatic group containing at least 8 carbon atoms. Preferably $Q^1$ and $Q^2$ are the same and are both groups of formula (III).

A most preferred example of compounds of formula (II) is 1,2-dipentacosanoyl-10,12-diyne-sn-glycero-3-phosphorylcholine (DAPC).

Compounds of formula (II) are suitable for coating hydrophobic substrates and after coating may be crosslinked intramolecularly or intermolecularly for example by irradiation as is described in EP-A-32622 the contents of which are incorporated herein by reference.

Alternatively compounds of formula (II) may be prepolymerised by intermolecular crosslinking so that an oligomer of a compound of formula (II) is used to treat the substrate. This pre-polymerisation process is described in more detail in our UK Patent Application WO-A-92/21386 the contents of which are incorporated herein by reference.

A.2 Non-polymeric compounds containing a group of formula (I)

Other non-polymeric compounds which may be used in the method of the present invention include those of formula (IV):

wherein Y is a reactive group which can form a covalent bond with a reactive group on the surface of a material and Z is a group of formula (I) as hereinbefore defined.

As examples of the reactive group Y there may be mentioned groups which will react with surface hydroxyl groups of a material, for instance halogen, haloalkyl, halo-dialkylsilyl, halo(dialkyl)silylalkyl, aminoalkyl and activated aminoalkyl groups. In such groups the alkyl chain where present may be interrupted by one or more etheric oxygen atoms and/or aromatic, e.g. phenyl rings. Such compounds are described in more detail in EP-A-157469.

A.2.1 Among the compounds of formula (IV), an especially preferred group of compound for use in the present invention are those in which the reactive group Y is a group of formula (V):

in which W is hydrogen or —NHW is an activated amine group capable of reacting with a surface, and X is a straight or branched $C_{1-20}$ alkylene group, preferably a group of formula $-(CH_2)_b-$, or X is a group of formula $-(CH_2CH_2O)_c-$, or $-(CH_2)_d-Ar-(CH_2)_e-$ where b is from 1 to 20, c is from 1 to 20, d and e are the same or different and each is from 0 to 5, and Ar is a para- or meta-disubstituted phenyl group (preferably a para-disubstituted phenyl group) which is optionally further substituted by one or more $C_1$–$C_4$ alkyl groups, or an acid addition salt thereof or a hydrate thereof.

Where —NHW is an activated amine group capable of reacting with a surface, preferably W is:

a group B—C(O)— where B is halogen, an alkyl group, preferably containing one to four carbon atoms, unsubstituted or substituted by one or more electron withdrawing substituents, a phenyl or 5- or 6-membered heteroaromatic ring containing from 1 to 3 nitrogen atoms, optionally fused with a further phenyl ring or 5- or 6-membered heteroaromatic ring containing 1 to 3 nitrogen atoms and unsubstituted or substituted by one or more electron withdrawing substituents;

a group $B^1$—OC(O)— where $B^1$ is an alkyl group, preferably containing one to four carbon atoms, unsubstituted or substituted by one or more electron withdrawing substituents or is a phenyl or 5- or 6-membered heteroaromatic ring containing 1 to 3 nitrogen atoms, optionally fused with a further phenyl ring or 5- or 6-membered heteroaromatic ring containing 1 to 3 nitrogen atoms and unsubstituted or substituted by one or more electron withdrawing substituents; or a phenyl or 5- or 6-membered heteroaromatic ring containing 1 to 3 nitrogen atoms optionally fused with a further phenyl ring or 5- or 6-membered heteroaromatic ring containing 1 to 3 nitrogen atoms and unsubstituted or substituted by one or more electron withdrawing substituents.

Suitable electron withdrawing substituents, which may be present in the group W, include halogen, nitro and cyano.

Where the group W contains a heteroaromatic ring, preferably the heteroaromatic ring is an imidazole or 1,3,5-benzotriazole.

Particularly preferred compounds containing a group of formula (V) are those in which X is —$(CH_2)_b$— and b is from 1 to 8, especially 2 to 6. Other preferred compounds are those wherein X is —$(CH_2CH_2O)_c$— and c is from 1 to 7.

Compounds containing a group of formula (V) are suitable for treating a substrate having reactive groups at the surface, such as carboxyl, hydroxyl, amino or thiol groups, if necessary using a prior activation of a the substrate. The use of these compounds is described in more detail in our earlier unpublished patent application WO-A-92/07858.

A2.2 Further compounds which may be used to treat the surfaces of synthetic polymers according to the invention are those of formula (IV) in which the group Y is a group —$(CH_2)_e$V, —$(CH_2)_f$—Ar—$(CH_2)_g$V, —$(CH_2CH_2O)_b$V or —$CH_2$—CHV—$CH_2$V wherein e is from 1 to 30, Ar is a para- or meta-disubstituted aryl or heteroaryl group;

f and g are the same or different and each is from 0 to 5, and f+g is from 1 to 10;

h is from 1 to 20 and

V is a group which reacts with functional groups of the polymer.

Preferably in such compounds V is:

an epoxide group;

a group

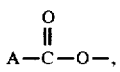

where A is $C_{1-4}$ straight or branched alkyl optionally substituted with one or more electron withdrawing groups or A is an optionally substituted aromatic or heteroaromatic ring system;

a group $T^1$—$SO_3$—, where $T^1$ is a straight chain alkyl of 1 to 4 carbon atoms optionally substituted by alkyl or alkoxy of 1 to 4 carbon atoms or halogen or an optionally substituted aromatic or heteroaromatic ring system;

a group

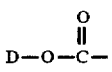

where D is an optionally substituted aromatic or heteroaromatic ring system or an N-substituted imide derivative;

a group

where E is a halogen atom, or an N-substituted nitrogen-containing heteroaromatic ring system; or a group of formula RC(O)OC(O)—, where R' is a group Z—$(CH_2)_e$—, Z—$(CH_2CH_2O)_h$— or Z—$(CH_2)_f$—Ar—$(CH_2)_g$— where Z is a group of formula (I), e, f, g, and h are as hereinbefore defined, or R' is an alkyl group preferably of 1 to 4 carbon atoms, optionally substituted by alkyl or alkoxy of 1 to 4 carbon atoms or halogen or is an optionally substituted aromatic or heteroaromatic ring system.

These compounds are particularly suitable for treating polymer substrates having free reactive hydroxyl, carboxyl, or amino groups. In other cases it may be necessary to activate the substrate prior to reaction with these compounds using known etching or derivatising techniques. It may also be desirable in certain cases to provide spacer groups between the polymer and the residue of a compound of formula (IV). The use of the compounds described under A3 is described in more detail in WO-A-91/13639 the contents of which are incorporated herein by reference.

A2.3 Further compounds of the formula (IV) which may be mentioned are thiol and disulphide compounds in which the reactive group Y is a group of formula (VI)

U—S—T—$X^1$— (VI)

in which $X^1$ is a straight or branched $C_{1-20}$ alkylene group, preferably a group of formula —$(CH_2)_{ba}$—, or $X^1$ is a group of formula —$(CH_2CH_2O)_{ea}$—, or —$(CH_2)_{da}$—Ar—$(CH_2)_{ea}$— where ba is from 1 to 30, ca is from 1 to 20, da and ea are the same or different and each is from 0 to 5, and Ar is a para- or meta-disubstituted aryl group such as a phenyl, biphenyl or naphthyl group (preferably a para-disubstituted biphenyl group) which is optionally further substituted by one or more $C_1$–$C_4$ alkyl groups; and either T is a valence bond or a divalent functional or heterocyclic group; and U is hydrogen or a group —SU$^1$ where U$^1$ is an alkyl, cycloalkyl, alkylcycloalkyl, aryl, alkylaryl, heterocyclic, alkylheterocyclic group or a group of formula (VII):

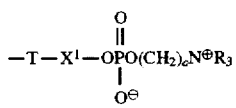
(VII)

where T, X$^1$, R and a are as hereinbefore defined; or

T is a trivalent alkylene group, and

U is a group —SU$^1$ and U$^1$ is an alkylene group, unsubstituted or substituted by alkyl, aryl, alkylaryl, cycloalkyl or alkylcycloalkyl groups and bonded to the group T so —T—S—S—U$^1$ form a 5 to 8 membered, preferably 5 or 6 membered, ring containing a disulphide linkage;

or a hydrate thereof.

Compounds in which Y is a group of formula (VI) are particularly useful for the treatment of metal, e.g. silver, substrates. Their use is described in more detail in our UK patent application 9224031.6 filed 16 Nov. 1992 the contents of which are incorporated herein by reference.

B. Polymeric compounds containing a group of formula (I)

Polymers which may be used to provide a surface bearing pendant groups of formula (I) include polymers which are obtainable by polymerising or copolymerising a polymerisable compound containing a group of formula (I), and polymers which are obtainable by grafting, e.g. polymerisation grafting, of a compound containing a group of formula (I), e.g. a polymerisable compound, onto a polymer substrate.

Such a polymer may be a homopolymer or copolymer of a polymerisable compound containing a group of formula (I). Alternatively a polymeric compound containing such groups may be a polymer onto which the groups of formula (I) have been grafted.

Such polymers may for example be condensation polymers such as polyesters, polyurethanes or polymers of ethylenically unsaturated compounds, such as polyolefins, poly(alk)acrylates for example polyacrylates or polymethacrylates, polystyrenes or polyvinyl polymers.

B1 One such type of polymeric compound, is a polymer obtainable by copolymerising a polymerisable, preferably ethylenically unsaturated, comonomer containing a group of formula (I) and a comonomer containing a group capable of binding the copolymer to a surface or by polymerising a polymerisable, preferably ethylenically unsaturated, monomer containing both a group of formula (II) and a group capable of binding the polymer to a surface. Such polymers which may be used to coat a surface of a substrate.

Preferably such comonomers are acrylates, alkacrylates, acrylamides, alkacrylamides or styrene derivatives which contain a group of formula (I) or a group capable of binding the polymer to a surface. Groups may bind to a surface by physisorption, covalent bonding or ionic bonding, e.g. by physisorption.

Preferably such copolymers contain residues of one or more comonomer derivatives of acrylic acid, alkacrylic acid or styrene of formula (VIII) or (IX).

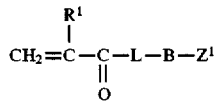
(VIII)

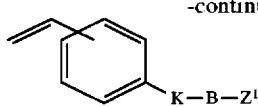
(IX)

in which

R$^1$ is hydrogen or a C$_1$–C$_4$ alkyl group;

L is —O— or —NR$^2$— where R$^2$ is hydrogen or a C$_1$–C$_4$ alkyl group or R$^2$ is —B—Z$^1$ where B and Z$^1$ are as defined below;

K is a group —(CH$_2$)$_p$OC(O)—, —(CH$_2$)$_p$C(O)O—, —(CH$_2$)$_p$OC(O)O—, —(CH$_2$)$_p$NR$^3$—, —(CH$_2$)$_p$NR$^3$C(O)—, —(CH$_2$)$_p$C(O)NR$^3$—, —(CH$_2$)$_p$NR$^3$C(O)O—, —(CH$_2$)$_p$OC(O)NR$^3$—, —(CH$_2$)$_p$NR$^3$C(O)NR$^3$—, (in which the groups R$^3$ are the same or different) —(CH$_2$)$_p$O—, —(CH$_2$)$_p$SO$_3$—, or, optionally in combination with B, a valence bond and p is from 1 to 12 and R$^3$ is hydrogen or a C$_1$–C$_4$ alkyl group;

B is a straight or branched alkylene, oxaalkylene or oligo-oxaalkylene chain, preferably containing up to 12 carbon atoms, optionally containing one or more fluorine atoms up to and including perfluorinated chains or, if Z$^1$ contains a carbon-carbon chain between B and the centre of permanent positive charge or if Y contains a terminal carbon atom bonded to B, a valence bond;

and Z$^1$ is a group of formula (I) or alternatively is a group of formula (X), (XI) or (XII).

The groups of formulae (X), (XI) and (XII) are:

(X)

(XI)

(XII)

wherein Z is a group of formula (I), R$^4$ is hydrogen or a group of formula —C(O)B$^1$R$^{4a}$ where R$^{4a}$ is hydrogen or methyl preferably methyl, B$^1$ is a valence bond or straight or branched alkylene, oxalkylene or oligo-oxaalkalyene group, preferably containing up to 12 carbon atoms; and if B is other than a valence bond, z is 1 and if B is a valence bond, z is O, when the group of formula (X), (XI) or (XII) is directly bonded to an oxygen or nitrogen atom and otherwise z is 1.

The proviso on whether B may be a valence bond ensures that the group of formula (I) is not directly bonded to a heteroatom, such as an oxygen or nitrogen atom.

Preferably Z$^1$ is a group of formula (I).

Such copolymers further comprise the residues of comonomers containing groups capable of binding the copolymer to a surface by physisorption, or by covalent binding to a reactive group at the surface or by ionic bonding. Specific examples of these comonomers are compounds of formulae (XIIIA) and (XIIIB)

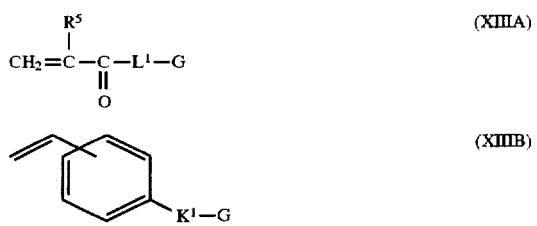

(XIIIA)

(XIIIB)

wherein $R^5$ is hydrogen or a $C_{1-4}$ alkyl group;

$L^1$ is —O— or —$NR^6$— where $R^6$ is hydrogen or a $C_{1-4}$ alkyl group or $R^6$ is —G as defined below:

$K^1$ is a group —$(CH_2)_qOC(O)$—, —$(CH_2)_qC(O)$—, —$(CH2)_qOC(O)O$—, —$(CH_2)_qNR^7$—, —$(CH_2)_qNR^7C(O)$—, —$(CH_2)_qC(O)NR^7$—, —$(CH_2)_qNR^7C(O)O$—, —$(CH_2)_q OC(O)NR^7$—, —$(CH_2)_qNR^7C(O)NR^7$—, (in which the groups $R^7$ are the same or different) —$(CH_2)_qO$—, —$(CH_2)_qSO_3$—, or, optionally in combination with B, a valence bond and q is from 1 to 12 and $R^7$ is hydrogen or a $C_1$–$C_4$ alkyl group, and G is a) a reactive group capable of covalently binding to a surface;

b) a group capable of binding to a surface by physisorption; or c) an ionic group capable of binding to a surface by ionic interaction.

In the case a), G may be for instance an alkylene, oxalkylene or oligo-oxaalkylene chain, preferably containing up to 12 carbon atoms, terminating in a reactive group such as aldehyde, hydroxyl, amino, carboxyl, epoxy, —$CHOHCH_2Hal$ (in which Hal is a halogen atom such as chlorine, bromine or iodine), succinimido, tosylate, such as 2(N-methylpyridinium tosylate), triflate, imidazole carbonyl-amino or an optionally substituted triazine.

Alternatively, in compounds of formula (XIIIA) —$L^1$—G may be a hydroxyl group; such compounds are acrylic or alkacrylic acids.

In addition the residues of such comonomers may be used to provide crosslinkable groups in the polymer. Such comonomers may also provide means for the attachment of a ligand to the polymer either before, or more preferably after, using the polymer to treat a surface.

In the case b) G may for instance be an alkyl, alkoxy-alkyl or (oligo-alkoxy)alkyl group containing 6 or more, preferably 6 to 24, carbon atoms, or an alkyl, alkoxy-alkyl or (oligo-alkoxy)alkyl group substituted by one or more fluorine atoms and preferably containing 6 or more, more preferably 6 to 24 carbon atom, or G may be a siloxy group typically containing from 1 to 50, preferably from 5 to 30 silicon atoms.

In the case c) G may for instance be a carboxylate, sulphonate, hydrogenphosphate or phosphate group when the surface has a cationic surface charge or a quaternary ammonium or phosphonium group where the surface has an anionic surface charge.

Such copolymers may further comprise the residues of one or more diluent comonomers.

Particular examples of diluent comonomers include alkyl (alk)acrylate preferably containing 1 to 4 carbon atoms in the alkyl group of the ester moiety, such as methyl (alk)acrylate; a dialkylamino alkyl(alk)acrylate, preferably containing 1 to 4 carbon atoms in each alkyl moiety of the amine and 1 to 4 carbon atoms in the alkylene chain, e.g. 2-(dimethylamino)ethyl (alk)acrylate; an alkyl (alk) acrylamide preferably containing 1 to 4 carbon atoms in the alkyl group of the amide moiety; a hydroxyalkyl (alk) acrylate preferably containing from 1 to 4 carbon atoms in the hydroxyalkyl moiety, e.g. a 2-hydroxyethyl (alk) acrylate; or a vinyl monomer such as an N-vinyl lactam, preferably containing from 5 to 7 atoms in the lactam ring, for instance vinyl pyrrolidone; styrene or a styrene derivative which for example is substituted on the phenyl ring by one or more alkyl groups containing from 1 to 6, preferably 1 to 4, carbon atoms, and/or by one or more halogen atoms, such as fluorine atoms, e.g. (pentafluorophenyl)styrene.

Other suitable diluent comonomers include polyhydroxyl, for example sugar, (alk)acrylates and (alk)acrylamides in which the alkyl group contains from 1 to 4 carbon atoms, e.g. sugar acrylates, methacrylates, ethacrylates, acrylamides, methacrylamides and ethacrylamides. Suitable sugars include glucose and sorbitol. Particularly suitable diluent comonomers include methacryloyl glucose or sorbitol methacrylate.

It is to be understood that throughout the specification (alk)acrylate, (alk)acrylic and (alk)acrylamide mean acrylate or alkacrylate, acrylic or alkacrylic and acrylamide or alkacrylamide respectively. Preferably unless otherwise stated alkacrylate, alkacrylic and alkacrylamide groups contain from 1 to 4 carbon atoms in the alkyl group thereof and are most preferably methacrylate, methacrylic or methacrylamide groups. Similarly (meth)acrylate, (meth)acrylic and (meth)acrylamide shall be understood to mean acrylate or methacrylate, acrylic or methacrylic and acrylamide or methacrylamide respectively.

Alternatively polymers may be used which comprise residues of compounds of formula (VIII) or (IX) in which the group —$Z^1$ is a group of formula (X) or (XI) but where —$B^1$ is a group capable of binding to a surface by physisorption such as alkylene, oxaalkylene or oligo-oxaalkylene, optionally substituted by one or more fluorine atoms and preferably containing up to 24, more preferably from 6 to 18 carbon atoms or a siloxane group. Such monomers contain both a group of formula (I) and a group capable of providing to a surface by physisorption, and may be used in homopolymers or in copolymers with other comonomers either containing a group of formula (I) such as those of formula (VIII) or (IX) or capable of providing physisorption such as those of formula (XIIIA) or (XIIIB) and/or optionally one or more diluent comonomers.

It will be appreciated that polymers or copolymers containing groups capable of binding to a surface by physisorption are particularly suitable for treating hydrophobic surfaces. Similarly copolymers containing groups capable of covalently binding to a surface are suitable for binding to surface having reactive groups such as hydroxyl, carboxyl or amino groups; such surfaces are generally hydrophilic.

Polymers and copolymers containing residues of a polymerisable compound containing a group of formula (I) have been described in more detail in our earlier Patent Application WO-A-93/01221 the contents of which are incorporated herein by reference.

B2 Further polymeric compounds which may be used to treat a substrate include polymers obtainable by grafting a compound containing a group of formula (I) onto a polymer substrate. Where necessary an intermediate binding group may be used which is first grafted onto the polymer and then reacts with the compound containing the group of formula (I).

Compounds which may be used to graft a group of formula (I) onto a polymer include compounds of formula (XIV)

$$Y^3—X^3—Z \qquad (XIV)$$

in which Z is a group of formula (I), $X^3$ is an aryl or a straight or branched $C_1$–$C_{20}$ alkylene group, optionally containing one or more carbon-carbon double or triple bonds, ether linkages or aryl groups; the aryl groups being unsubstituted or substituted by one or more $C_{1-4}$ alkyl groups; and $Y^3$ is a reactive group.

For example $Y^3$ may be an amino or hydroxyl group, a group $HOCH_2CH(OH)$— (in which case $X^3$ is preferably —$CH_2$—, so that the compound of formula (I) is a glycerophosphate) or an imidazole group.

Alternative $Y^3$ may be a polymerisable group capable of polymerisation initiated by a radical forming linking group bound to the polymer. Where $Y^3$ is such a group then the compound of formula (XIV) may be a compound of formula (XV) or (XVI):

$$\begin{array}{c} R^8 \\ | \\ CH_2=C-C-L-X^3-Z \\ \| \\ O \end{array} \quad (XV)$$

$$\text{(XVI)} \quad \text{[styrene-like structure]}-K^2-X^2-Z$$

in which Z is a group of formula (I), $X^3$ is defined in relation to formula (XIV) and $R^8$ is hydrogen or a $C_1$-$C_4$ alkyl group;

$L^2$ is —O— or —$NR^9$— where $R^9$ is hydrogen or a $C_1$-$C_4$ alkyl group or $R^9$ is —$X^3$—Z where $X^3$ and Z are as defined above; and $K^2$ is a group —$(CH_2)_rOC(O)$—, —$(CH_2)_rC(O)O$—, —$(CH_2)_rOC(O)O$—, —$(CH_2)_rNR^{10}$—, —$(CH_2)_rNR^{10}C(O)$—, —$(CH_2)_rC(O)NR^{10}$—, —$(CH_2)_rNR^{10}C(O)O$—, —$(CH_2)_rOC(O)NR^{10}$—, —$(CH_2)_rNR^{10}C(O)NR^3$—, (in which the groups $R^{10}$ are the same or different) —$(CH_2)_rO$—, —$(CH_2)_rSO_3$—, or a valence bond and r is from 1 to 12 and $R^{10}$ is hydrogen or a $C_1$-$C_4$ alkyl group.

Compounds such as those of formula (XIV) may be used to treat polymers such as polyurethanes, hydroxyethyl methacrylates and hydroxyethyl methacrylate/methacrylic acid hydrogels, cellulose and cellulose derivatives, polyvinyldifluoride, polypropylenes, polyamides and polyimides. Most particularly this technique may be used to graft groups of formula (I) onto polyurethanes.

Grafted polymers produced in this way may then be used to treat or coat a substrate according to the present invention. Alternatively in some cases such polymers may be moulded to form a bulk material rather than being used to treat a substrate.

The use of such grafted polymers is described in more detail in our earlier Patent Application WO-A-93/0508 the contents of which are incorporated herein by reference.

B3 Further polymers which may be used in the method of the present invention are crosslinked copolymers obtainable by copolymerising a neutral diluent monomer or monomers, a polymerisable monomer or monomers containing a group of formula (I) and a bifunctional or trifunctional crosslinking agent.

Preferred monomers containing a group of formula (I) are those of formula (VIII) or (IX) as hereinbefore defined.

Preferred diluent monomers include alkyl (alk)acrylates, dialkylamino alkyl (alk)acrylates, alkyl(alk)acrylamides, hydroxyalkyl (alk)acrylates, N-vinyl lactams, styrene, substituted styrene derivatives; and mixtures thereof, preferably containing 1 to 4 carbon atoms in the said alkyl groups and moieties. More especially preferred as diluent monomers are vinylpyrrolidone, 2-hydroxyethylmethacrylate, methylmethacrylate and mixtures thereof.

Conventional crosslinking agents may be used. Examples of suitable crosslinking comonomers include alkane diol or triol di- or tri(alk)acrylates, e.g. (meth)acrylates, preferably containing 1 to 8 carbon atoms in the diol or triol residue; alkylene di- or tri-(alk)acrylamides, e.g. (meth)acrylamides, preferably containing 1 to 6 carbon atoms in the alkylene group and di- or tri-vinyl compounds such as di- or tri-vinyl benzene compounds. Particular examples of crosslinking agents include ethyleneglycoldimethacrylate, tetraethyleneglycol dimethacrylate, trimethylolpropanetrimethacrylate and N,N-methylenebisacrylamide.

Such copolymers are disclosed in our earlier patent application WO-A-92/07885 the contents of which are incorporated herein by reference as being suitable for use in contact lenses which are subject to reduced protein deposits, and in the context of the present invention such polymers may be used as coatings or in bulk to reduce adhesion of microorganisms.

B4 Further polymers which may be used in the method of the present invention include polyurethanes obtainable by the reaction of an aliphatic or aromatic di- or polyisocyanate and a diol or polyol having at least two hydroxyl groups capable of reacting with a isocyanate group and having the residue of at least one further hydroxyl group present as a group of formula (I).

Such polyurethane polymers may be used in the fabrication of materials, having a reduced rate of microorganism adhesion, using conventional techniques such as moulding. These polymers are described in more detail in WO-A-86/02933 the contents of which are incorporated herein by reference.

B5. Further polymers which may be used in the method of the present invention are polyesters derived from a glycerol having the residue of one of the hydroxyl groups present as a group of formula (I) and at one di- or polyfunctional acid or acid derivative thereof.

Preferred polyesters include repeating units of the formula (XVII)

$$\begin{array}{c} CH_2-Z \\ | \\ -C-O-CH \\ | \\ CH_2-O-C-X^4- \\ \| \\ O \end{array} \quad (XVII)$$

in which Z is a group of formula (I) and $X^4$ is a straight or branched $C_{1-15}$ alkylene or $C_{2-15}$ alkenylene group. Preferably such polymers are linear.

Such polyesters may be used to form materials subject to a reduced rate of microorganism adhesion using conventional techniques such as moulding. The polymers are described in more detail in WO-A-88/00956 the contents of which are incorporated herein by reference.

B6. Further polymeric materials which may be used in the method of the present invention are plastics materials which comprise a polymer and a lipid which comprises a group of formula (I).

In such a material, the lipid may be used as an additive for the polymer and in addition it may serve to reduce the adhesion of microorganisms to the polymer. A wide variety of polymers may be used.

Preferably, such a lipid is a phospholipid containing a group of formula (I), and most preferably, an analogue of a fatty acid diester of phosphatidyl choline of formula (VI).

Such materials are described in more detail and may be produced in the manner described in WO-A-87/02684.

From the above it will be appreciated that a large number of different types of compounds containing groups of formula (I) may be used in the method of the present invention, either to treat an existing substrate to reduce microorganism adhesion or to fabricate a bulk material showing reduced microorganism adhesion.

It will further be appreciated that when a substrate is treated with a compound containing a group of formula (I), the nature of the treatment used will depend upon the nature of the substrate.

Compounds containing groups of formula (I) which bind to the substrate by physisorption are particularly suitable for coating hydrophobic surfaces, e.g. polyethylene, polypropylene and polytetrafluoroethylene (PTFE) surfaces.

Hydrophilic surfaces may be rendered hydrophobic and suitable for coating with such compounds by known methods (see for example "Chemical Reactions of Polymers" Ed. E. M. Fettes, 1964, Interscience, London).

Treatment with such a compound is generally carried out by coating the surface with a solution or dispersion of the compound, generally in an alcoholic, aqueous, organic or halogenated solvent or a mixture thereof, e.g. methanol, ethanol, dichloromethane or freon. The treatment is generally carried out at ambient or elevated temperature, such as from 5° to 60° C.

Compounds containing groups of formula (I) and a group capable of binding the polymer to a surface covalently are particularly suitable for treating substrates having functional groups, such as hydroxyl, carboxyl or amino groups.

Where necessary the surface of the substrate may be functionalised prior to treatment. For surfaces which do not have functional groups it is necessary to introduce these groups at the surface before treatment with the polymer. This can be effected by known etching or derivatising techniques, such as plasma discharge, which introduce the appropriate surface functionality (see for example "Chemical Reactions of Polymers" Ed. E. M. Fettes, 1964, Interscience, London).

In certain cases it is also necessary to activate functional groups at the surface of the substrate and/or the reactive groups of the polymer of the invention. This may be achieved by known means using a known activating agent for example a carbodiimide such as 1-ethyl-3-(3-dimethylaminopropyl)carbodiimide. Other suitable activating agents are disclosed in "Methods in Enzymology, volume 135, Immobilised Enzymes and Cells, part B", Ed. K. Mosbach, Academic Press Inc, New York, 1987.

Treatment with such a compound is generally carried out by treating the surface with a solution of the compound generally an alcoholic, aqueous alcoholic or aqueous solution. The treatment is generally carried out at a temperature from −5° to 50° C., for from 0.1 to 24 hours and at a pH from 2 to 13.

Materials having a surface comprising pendant groups of formula (I) can be used as a construction material for devices having many applications where microorganism adhesion can produce problems. One specific application is in relation to implants or prostheses for the human or animal body, particularly where these implants or prostheses are to come into direct physical contact with microorganisms. They can also be used in the construction of bioseparation membranes and other devices that are to be brought into contact with fluids containing microorganisms on an extra-corporeal basis.

When the method of the present invention is used to provide the surface of a material which is then used in the construction of a finished device, it may be necessary to take precautionary steps to ensure that the surface is not damaged and the effectiveness of the treatment is not reduced before the finished device is produced.

In addition, the method of the present invention can be used to treat finished devices such as implants, prostheses, membranes, catheters, contact lenses and many other articles to reduce microorganism adhesion to the article.

The present invention will now be further illustrated by the following Examples:

COMPARATIVE EXAMPLE (C1)

Samples of uncoated pieces of PVC tubing, all cut to the same length (1.5 cm) were incubated for two hours with gentle shaking in a physiological buffer containing $^{14}$C-thymidine radio-labelled bacteria and a serum supplement. After incubation, each sample was washed gently in fresh buffer and the adhering bacteria remaining were extracted and the radio-label measured in a scintillation counter. Results are expressed as counts per minute in Table 1 and relate directly to the number of bacterial cells on the surface.

Three different strains of *Staphylococcus epidermidis* (743,4777-II and 4560) and three different strains of *Staphylococcus aureus* (E1369, E2371 and E4485) have been employed which are commonly implicated in nosocomal infections in the clinic.

EXAMPLE 1

The Comparative Example was repeated but using PVC tubing coated with di-acetylenic phosphatidyl choline which was obtained by the procedure described in Reference Example 1. The results, expressed as counts per minute, are shown in Table 1 and Table 2 shows the adhesion as a percentage of the adhesion obtained for an untreated PVC tube, as in the Comparative Example.

EXAMPLE 2

The Comparative Example was repeated but using PVC tubing coated with a physisorbable copolymer of the type described under B1 [poly(2(methacryloyloxyethyl)-2' (trimethylammonium)ethyl phosphate inner salt- co-dodecyl methacrylate (1:4)] above which was obtained by a procedure analogous to that described in Reference Example 1. The results expressed as counts per minute are shown in Table 1 and Table 2 shows the adhesion as a percentage of the adhesion obtained for an untreated PVC tube, as in the Comparative Example.

These results demonstrate that, under conditions which are similar to those which might be encountered physiologically, significant reduction in bacterial adhesion, and frequently reduction of up to 80–90% in adhesion are observed.

TABLE 1

| Adhesion Expressed as Counts per Minute | | | |
|---|---|---|---|
| Strain | Comparative | Example 2 | Example 1 |
| 743 | *526 | 49 | 144 |
| 4777-II | 158 | 12 | 46 |
| 4560 | 1265 | 63 | 163 |
| E1369 | 854 | 32 | 194 |
| E2371 | 319 | 58 | 99 |
| E4485 | 195 | 50 | 45 |

*mean counts per minute (range of triplicates)

TABLE 2

| | Adhesion Expressed as Percentage of Uncoated Control | | |
|---|---|---|---|
| Strain | Comparative | Example 2 | Example 1 |
| 743 | 100 | 9 | 27 |
| 4777-II | 100 | 8 | 29 |
| 4560 | 100 | 5 | 13 |
| E1369 | 100 | 4 | 23 |
| E2371 | 100 | 18 | 31 |
| E4485 | 100 | 26 | 23 |

REFERENCE EXAMPLE 1
Treatment of PVC Tubing with DAPC

Samples of soft PVC tubing of the type which is used in extra-corporeal circuitry were either washed with warm ethanol or filtered deionised water and thoroughly dried prior to coating.

The tubing was coated, in a dust free area to avoid contamination, by pipetting the coating solution (prepolymerised diacetylenic phosphatidyl choline (DAPC) of the type described under A3 above, in ethanol (Analar) at 10 mg/ml) into the hollow tube and gently working the solution backwards and forwards (for sections up to 120 cm in length) until the whole of the inside of the tubing was evenly coated.

Excess coating solution was then allowed to drain into a collection bath and the tubing allowed to dry at room temperature.

We claim:

1. A method of reducing the adhesion of a bacterium to the surface of an article, comprising the step of providing on a surface of the article a compound having pendant groups of formula (I)

in which each group R is the same or different and is alkyl of 1 to 4 carbon atoms and a is from 1 to 4.

2. A method according to claim 1 in which in the groups of formula (I) the groups R are each methyl and a is 2.

3. A method according to claim 1 in which said surface has a coating of said compound containing a group of formula (I).

4. A method according to claim 3 in which the surface is coated with a compound which is a phospholipid or analogue thereof.

5. A method according to claim 4 in which the phospholipid is a fatty acid diester of phosphatidyl choline containing from 2 to 26 carbon atoms in each fatty acid side chain.

6. A method according to claim 4 in which the phospholipid analogue is a diacetylenic phospholipid of formula (II)

in which z is a group of formula (I) as defined in claim 1 and wherein at least one of $Q^1$ and $Q^2$ is a group of formula (III)

wherein k is 0 or 1, $X^2$ is an aliphatic or cycloaliphatic group, $Y^2$ is H or a monovalent aliphatic or cycloaliphatic group, the total number of carbon atoms in $X^2$ and $Y^2$ in each $Q^1$ and/or $Q^2$ being 8 to 26, and the other of $Q^1$ and $Q^2$ is either (a) the same or a different group of formula (VII) or (b) is an aliphatic or cycloaliphatic group containing at least 8 carbon atoms.

7. A method according to claim 1 in which pendant groups of formula (I) are provided by a polymeric compound obtained by polymerizing or copolymerizing a polymerizable compound containing a group of formula (I) or by graft polymerization of a polymerizable compound containing a group of formula (I) onto a polymeric substrate.

8. A method according to claim 7 in which pendant groups of formula (I) are provided by a polymer which is:

obtained by copolymerizing a polymerizable comonomer containing a group of formula (I) and a comonomer containing a group capable of binding the copolymer to a surface by physisorption, covalent bonding or ionic bonding; or obtained by polymerizing or copolymerizing a polymerizable compound containing a group of formula (I) and a group capable of binding the polymer to a surface by physisorption, covalent bonding or ionic bonding.

9. A method according to claim 8 in which the polymer is a copolymer obtained by copolymerizing:

(a) an acrylate, alkacrylate, acrylamide, alkacrylamide or styrene derivative containing a group of formula (I); and (b) an acrylate, alkacrylate, acrylamide, alkacrylamide or styrene derivative containing a group capable of binding to a surface by physisorption;

(c) and optionally one or more diluent comonomers selected from the group consisting of alkyl(alk) acrylates containing 1–4 carbon atoms in the alkyl group; dialkylaminoalkyl(alk)acrylates containing 1–4 carbon atoms in each alkyl group; alkyl(alk) acrylamides containing 1–4 carbon atoms in the alkyl groups; hydroxyalkyl(alk)acrylates containing from 1–4 carbon atoms in the hydroxyalkyl group; N-vinyllactams; styrene; styrene substituted on the phenyl ring by one or more $C_{1-6}$-alkyl groups or one or more halogen atoms; and sugar (alk)acrylates and sugar (alk)acrylamides.

10. A method according to claim 9 in which the comonomer (b) contains an alkyl group containing 6 or more carbon atoms as physisorbable group.

11. A method according to claim 7, in which the article comprises a bulk polymer obtained by polymerizing or copolymerizing a polymerizable compound containing a group of formula (I).

12. A method according to claim 7 in which said polymerizable compound has the formula (VIII)

in which $R^1$ is hydrogen or a $C_1$–$C_4$ alkyl group;

L is —O— or —$NR^2$—, wherein $R^2$ is hydrogen or a $C_1$–$C_4$ alkyl group or $R^2$ is —B—$Z^1$ where B and $Z^1$ are as defined below;

B is a straight or branched alkylene, oxaalkylene or oligo-oxaalkylene chain containing up to 12 carbon atoms, optionally containing one or more fluorine atoms up to and including perfluorinated chains or, if $Z^1$ contains a carbon-carbon chain between B and the center of permanent positive charge or if $Z^1$ contains a terminal carbon atom bonded to B, a valence bond; and $Z^1$ is a group of formula (I).

13. A method according to claim 11, in which said polymerizable compound has the formula (VIII)

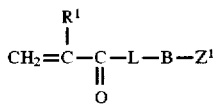
(VIII)

in which $R^1$ is hydrogen or a $C_1$–$C_4$ alkyl group;

L is —O— or —$NR^2$—, wherein $R^2$ is hydrogen or a $C_1$–$C_4$ alkyl group or $R^2$ is —B—$Z^1$ where B and $Z^1$ are as defined below;

B is a straight or branched alkylene, oxaalkylene or oligo-oxaalkylene chain containing up to 12 carbon atoms, optionally containing one or more fluorine atoms up to and including perfluorinated chains or, if $Z^1$ contains a carbon-carbon chain between B and the center of permanent positive charge or if $Z^1$ contains a terminal carbon atom bonded to B, a valence bond; and $Z^1$ is a group of formula (I).

14. A method in which the surface of an article is contacted with a bacterium-containing fluid and the adhesion of said bacterium to said surface is reduced by the presence at said surface of a compound having pendant groups of formula (I)

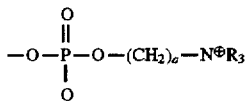
(I)

in which each group R is the same or different and is alkyl of 1 to 4 carbon atoms and a is from 1 to 4.

15. A method of reducing the adhesion of a bacterium to the surface of an in-dwelling catheter, comprising the step of providing on the surface of the in-dwelling catheter, a compound having pendant groups of formula (I)

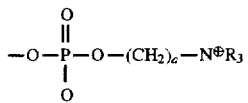
(I)

in which each group R is the same or different and is alkyl of 1 to 4 carbon atoms and a is from 1 to 4.

16. A method of reducing the adhesion of a bacterium to the surface of an article selected from the group consisting of a wound dressing, an article used in dentistry, an article used in marine shipping and an article used in freshwater shipping, comprising the step of providing on the surface of the article, a compound having pendant groups of formula (I)

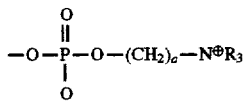
(I)

in which each group R is the same or different and is alkyl of 1 to 4 carbon atoms and a is from 1 to 4.

17. A method according to claim 3 wherein the pendant groups of formula (I) are provided by treating the surface with a non-polymeric compound containing a group of formula (I) and containing a reactive group which can form a covalent bond with a reactive group on the surface.

* * * * *

UNITED STATES PATENT AND TRADEMARK OFFICE
CERTIFICATE OF CORRECTION

PATENT NO. : 5,798,117
DATED : August 25, 1998
INVENTOR(S) : Roger R.C. New, et al.

It is certified that error appears in the above-identified patent and that said Letters Patent is hereby corrected as shown below:

Column 4, line 13, delete "—$(CO)_k$—$X^2$—$C\equiv C$—$\equiv C$—$Y^2$" and insert -- —$(CO)_k$—$X^2$—$C\equiv C$—$C\equiv C$—$Y^2$--.

Column 5, line 54, delete "—$(CH_2CH_2O)bV$" and insert

-- —$(CH_2CH_2O)_hV$--.

Column 6, line 59, delete "—$(CH_2CH_2O)_{ea}$—" and insert

-- —$(CH_2CH_2O)_{ca}$— --.

Column 9, line 14, delete "—$(CH2)_qOC(O)O$—" and insert

-- —$(CH_2)_qOC(O)O$— --.

UNITED STATES PATENT AND TRADEMARK OFFICE
CERTIFICATE OF CORRECTION

PATENT NO. : 5,798,117  Page 2 of 6
DATED : August 25, 1998
INVENTOR(S) : Roger R.C. New, et al.

It is certified that error appears in the above-identified patent and that said Letters Patent is hereby corrected as shown below:

Column 11, line 16, delete

"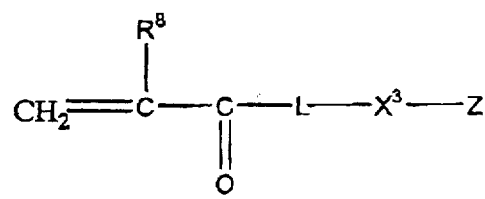"

and insert

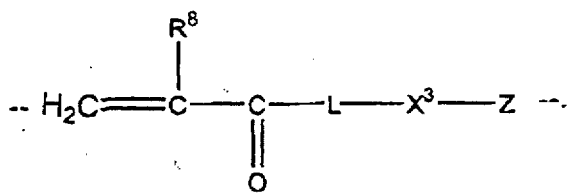

UNITED STATES PATENT AND TRADEMARK OFFICE
CERTIFICATE OF CORRECTION

PATENT NO. : 5,798,117
DATED : August 25, 1998
INVENTOR(S) : Roger R.C. New, et al.

It is certified that error appears in the above-identified patent and that said Letters Patent is hereby corrected as shown below:

In Column 15, line 39, delete

"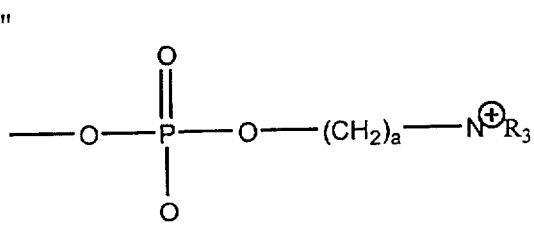"

and insert

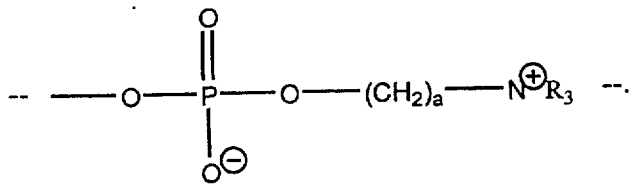 --.

UNITED STATES PATENT AND TRADEMARK OFFICE
CERTIFICATE OF CORRECTION

PATENT NO. : 5,798,117
DATED : August 25, 1998
INVENTOR(S) : Roger R.C. New, et al.

It is certified that error appears in the above-identified patent and that said Letters Patent is hereby corrected as shown below:

Column 15, lines 65, delete "—$(CO)_k$—$X^2$—C≡C—≡C—$Y^2$" and insert

-- —$(CO)_k$—$X^2$—C≡C—C≡C—$Y^2$--.

Column 17, line 32, delete

"
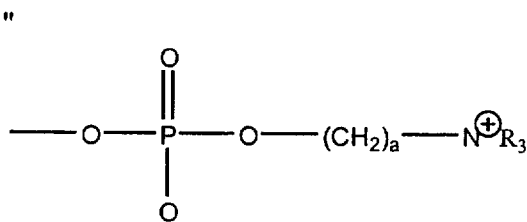
"

and insert

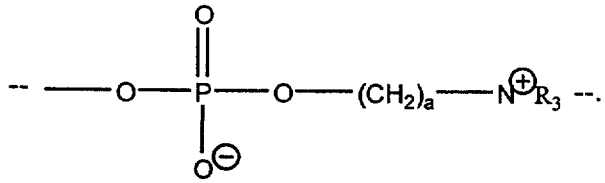

UNITED STATES PATENT AND TRADEMARK OFFICE
CERTIFICATE OF CORRECTION

PATENT NO. : 5,798,117
DATED : August 25, 1998
INVENTOR(S) : Roger R.C. New, et al.

It is certified that error appears in the above-identified patent and that said Letters Patent is hereby corrected as shown below:

Column 18, line 8, delete "

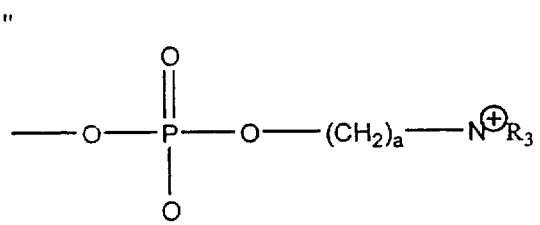

"

and insert

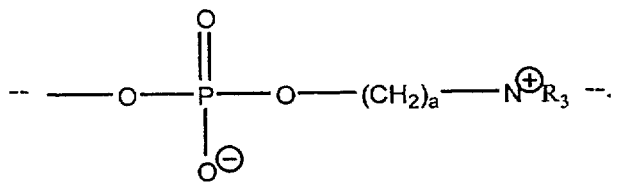

UNITED STATES PATENT AND TRADEMARK OFFICE
CERTIFICATE OF CORRECTION

PATENT NO. : 5,798,117  
DATED : August 25, 1998  
INVENTOR(S) : Roger R.C. New, et al.

Page 6 of 6

It is certified that error appears in the above-identified patent and that said Letters Patent is hereby corrected as shown below:

Column 18, line 23, delete

"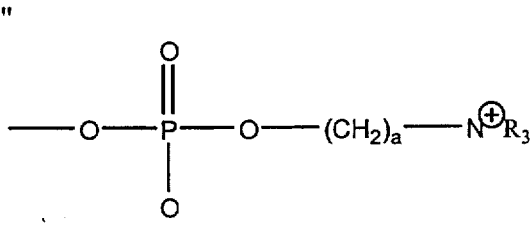"

and insert

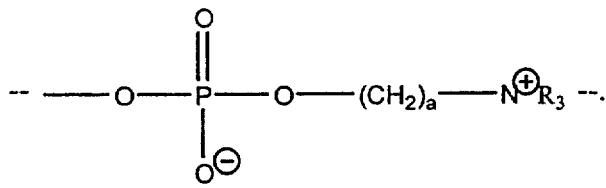

Signed and Sealed this

Twenty-third Day of May, 2000

Attest:

Q. TODD DICKINSON

*Attesting Officer*  *Director of Patents and Trademarks*